much lower activity than 1α,25-dihydroxy-vitamin $D_3$

United States Patent [19]

DeLuca et al.

[11] Patent Number: 5,194,431
[45] Date of Patent: Mar. 16, 1993

[54] 24-CYCLOPROPANE VITAMIN D DERIVATIVES

[75] Inventors: Hector F. DeLuca, Deerfield; Naoshi Nakagawa, Madison, both of Wis.

[73] Assignee: Wisconsin Alumni Research Foundation, Madison, Wis.

[21] Appl. No.: 910,423

[22] Filed: Jul. 8, 1992

[51] Int. Cl.$^5$ .................. C01J 172/00; C01J 9/00; A61K 31/59
[52] U.S. Cl. .................... 514/167; 552/541; 552/653
[58] Field of Search .............. 552/653, 508, 541; 514/167

[56] References Cited

U.S. PATENT DOCUMENTS

| | | | |
|---|---|---|---|
| 3,833,622 | 9/1974 | Babcock et al. | 552/653 |
| 3,901,928 | 8/1975 | Hesse et al. | 552/653 |
| 4,225,596 | 9/1980 | DeLuca et al. | 552/653 |
| 4,588,716 | 5/1986 | DeLuca et al. | 552/653 |
| 4,769,181 | 9/1988 | DeLuca et al. | 552/653 |
| 4,851,401 | 7/1989 | DeLuca et al. | 552/653 |
| 4,973,584 | 11/1990 | DeLuca et al. | 552/653 |

FOREIGN PATENT DOCUMENTS

WO89/10351 11/1989 PCT Int'l Appl. .

Primary Examiner—Marianne M. Cintins
Assistant Examiner—Kimberly J. Kestler
Attorney, Agent, or Firm—Andrus, Sceales, Starke and Sawall

[57] ABSTRACT

Vitamin $D_2$ analogs in which a cyclopropane ring is introduced onto the 24-carbon of the side chain of 1α,25-dihydroxyvitamin $D_2$ and 1α-hydroxyvitamin $D_2$. The compounds are characterized by a marked intestinal calcium transport activity while exhibiting much lower activity than 1α,25-dihydroxy-vitamin $D_3$ in their ability to mobilize calcium from bone. Because of their preferential calcemic activity, these compounds would be useful for the treatment of diseases where bone formation is desirbed, such as osteoporosis.

16 Claims, No Drawings

24-CYCLOPROPANE VITAMIN D DERIVATIVES

BACKGROUND OF THE INVENTION

This invention relates to biologically active vitamin D compounds. More specifically, the invention relates to 24-cyclopropane vitamin D compounds, to a general process for their preparation, and to their use in treating osteoporosis.

With the discovery of 1α,25-dihydroxyvitamin $D_3$ as the active form of the vitamin has come an intense investigation of analogs of this hormonal form of vitamin D with the intent of finding analogs that have selective activity. By now, several compounds have been discovered which carry out the differentiative role of 1,25-dihydroxyvitamin $D_3$ while having little or no calcium activity. Additionally, other compounds have been found that have minimal activities in the mobilization of calcium from bone while having significant activities in stimulating intestinal calcium transport. Modification of the vitamin D side chain by lengthening it at the 24-carbon has resulted in loss of calcium activity and either an enhancement or undisturbed differentiative activity. Placing the 24-methyl of 1α,25-dihydroxyvitamin $D_2$ in the epi-configuration appears to diminish activity in the mobilization of calcium from bone. On the other hand, increased hydrophobicity on the 26- and 27-carbons seems to increase the total activity of the vitamin D compounds provided the 25-hydroxyl is present.

Several of these known compounds exhibit highly potent activity in vivo or in vitro, and possess advantageous activity profiles and thus are in use, or have been proposed for use, in the treatment of a variety of diseases such as renal osteodystrophy, vitamin D-resistant rickets, osteoporosis, psoriasis, and certain malignancies.

It is well known that females at the time of menopause suffer a marked loss of bone mass giving rise ultimately to osteopenia, which in turn gives rise to spontaneous crush fractures of the vertebrae and fractures of the long bones. This disease is generally known as postmenopausal osteoporosis and presents a major medical problem, both in the United States and most other countries where the life-span of females reaches ages of at least 60 and 70 years. Generally, the disease which is often accompanied by bone pain and decreased physical activity, is diagnosed by one or two vertebral crush fractures with evidence of diminished bone mass. It is known that this disease is accompanied by diminished ability to absorb calcium, decreased levels of sex hormones, especially estrogen and androgen, and a negative calcium balance.

Similar symptoms of bone loss characterize senile osteoporosis and steroid-induced osteoporosis, the latter being a recognized result of long term glucocorticoid (cortico-steroid) therapy for certain disease states.

Methods for treating the disease have varied considerably but to date no totally satisfactory treatment is yet known. A conventional treatment is to administer a calcium supplement to the patient. However, calcium supplementation by itself has not been successful in preventing or curing the disease. Another conventional treatment is the injection of sex hormones, especially estrogen, which has been reported to be effective in preventing the rapid loss of bone mass experienced in postmenopausal women. This technique, however, has been complicated by the fear of its possible carcinogenicity. Other treatments for which variable results have been reported, have included a combination of vitamin D in large doses, calcium and fluoride. The primary problem with this approach is that fluoride induces structurally unsound bone, called woven bone, and in addition, produces a number of side effects such as increased incidence of fractures and gastrointestinal reaction to the large amounts of fluoride administered. Another suggested method is to block bone resorption by injecting calcitonin or providing phosphonates.

U.S. Pat. No. 4,225,596 suggests the use of various metabolites of vitamin $D_3$ for increasing calcium absorption and retention within the body of mammals displaying evidence of or having a physiological tendency toward loss of bone mass. The metabolites specifically named in that patent, i.e., 1α-hydroxyvitamin $D_3$, 1α-hydroxyvitamin $D_2$, 1α,25-dihydroxyvitamin $D_3$,1α,25-dihydroxyvitamin $D_2$ and 1,24,25-trihydroxyvitamin $D_3$, although capable of the activity described and claimed in that patent, are also characterized by the disadvantage of causing hypercalcemia, especially if used with the conventional calcium supplement treatment. Therefore, use of these compounds to treat osteoporosis has not been widely accepted. U.S. Pat. Nos. 3,833,622 and 3,901,928 respectively suggest using the hydrate of 25-hydroxyvitamin $D_3$ and 1α-hydroxyvitamin $D_3$ for treatment of osteoporosis in a general expression of utility for those compounds. It is well known that both of those compounds express traditional vitamin D-like activity, including the danger of hypercalcemia.

U.S. Pat. No. 4,588,716 also suggests the use of 1α,25-dihydroxy-24-epi-vitamin $D_2$ to treat bone disorders characterized by the loss of bone mass, such as osteoporosis. Although this compound expresses some of the vitamin D-like characteristics affecting calcium metabolism such as increasing intestinal calcium transport and stimulating the mineralization of new bone, it has the advantage of minimal effectiveness in mobilizing calcium from bone. The 24-epi compound may be administered alone or in combination with a bone mobilization-inducing compound such as a hormone or vitamin D compound such as 1α-hydroxyvitamin $D_3$ or $-D_2$, or 1α,25-dihydroxyvitamin $D_3$ or $-D_2$.

SUMMARY OF THE INVENTION

The present invention provides novel compounds exhibiting a desired, and highly advantageous, pattern of biological activity. These compounds are characterized by a marked intestinal calcium transport activity, as compared to that of 1α,25-dihydroxyvitamin $D_3$, while exhibiting much lower activity than 1α,25-dihydroxyvitamin $D_3$ in their ability to mobilize calcium from bone. Hence, these compounds are highly specific in their calcemic activity. Their preferential activity on intestinal calcium transport and reduced calcium mobilizing activity in bone allows the in vivo administration of these compounds for the treatment of metabolic bone diseases where bone loss is a major concern. Because of their preferential calcemic activity, these compounds would be preferred therapeutic agents for the treatment of diseases where bone formation is desired, such as osteoporosis, osteomalacia and renal osteodystrophy.

Structurally, the key feature of the compounds having these desirable biological attributes is that they are analogs of 1α-hydroxyvitamin $D_2$ and 1,25-dihydroxyvitamin $D_2$ in which a cyclopropane ring is introduced onto the 24 carbon of the side chain. Thus, the compounds of this type are characterized by the following general structure:

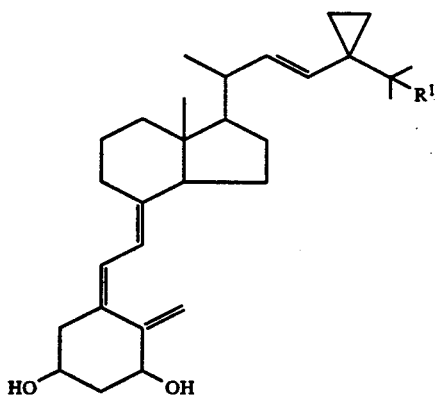

where $R^1$ may be hydrogen or hydroxy. The present invention, therefore, provides novel compounds showing preferential activity on intestinal calcium transport and reduced calcium mobilizing activity in bone, and are useful for the treatment of metabolic bone disease, such as osteoporosis, where bone loss is a major concern. More specifically, the compounds are 24,28-methylene-1α,25-dihydroxyvitamin $D_2$ and 24,28-methylene-1α-hydroxyvitamin $D_2$.

This invention also provides novel intermediate compounds formed during the synthesis of the end products. Structurally, the intermediate compounds are characterized by the following general structure:

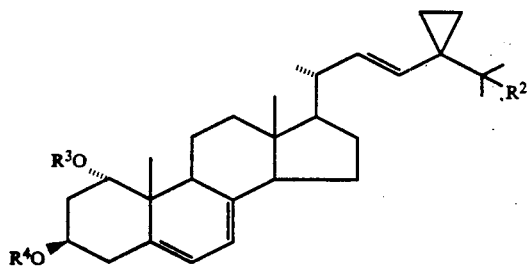

where $R^2$ may be hydrogen or hydroxy, $R^3$ may be a hydroxy-protecting group, and $R^4$ may be hydrogen or a hydroxy-protecting group.

In another aspect of the invention, it has now been found that the loss of bone mass, which is characteristic of osteoporosis may be effectively treated by the administration of a 24-cyclopropane vitamin $D_2$ compound in sufficient amounts to increase bone mass. More specifically, a method of treating osteoporosis comprises the administration of an effective amount of either 24,28-methylene-1α,25-dihydroxyvitamin $D_2$ or 24,28-methylene-1α-hydroxyvitamin $D_2$. The above compounds may be administered alone or in combination with other pharmaceutically acceptable agents. Dosages of from not less than about 0.5 μg/day to not more than about 50 μg/day of the individual compound per se, or in combinations, are generally effective. This method has the distinct advantage that it will restore bone mass due to the insignificant bone mobilization activity of this compound and further this compound advantageously will not cause hypercalcemia even if the compound is administered continuously on a daily basis, as long as the appropriate compound dosages are used, it being understood that the dosage levels will be adjusted dependent on the response of the subject as monitored by methods known to those skilled in the art.

The above method, involving the administration of the indicated dosages of 24,28-methylene-1α,25-dihydroxyvitamin $D_2$ or 24,28-methylene-1α-hydroxyvitamin $D_2$ is effective in restoring or maintaining bone mass, and thus provides a novel method for the treatment or prevention of various forms of osteoporosis such as postmenopausal osteoporosis, senile osteoporosis and steroid-induced osteoporosis. It will be evident that the method will find ready application for the prevention or treatment of disease states other than those named, in which the loss of bone mass is an indication.

DETAILED DESCRIPTION OF THE INVENTION

As used in the description and in the claims, the term hydroxy-protecting group signifies any group commonly used for the temporary protection of hydroxy functions, such as for example, alkoxycarbonyl, acyl, alkylsilyl, and alkoxyalkyl groups, and a protected hydroxy group is a hydroxy function derivatized by such a protecting group. Alkoxycarbonyl protecting groups are groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term 'acyl' signifies an alkanoyl group of 1 to 6 carbons, in all of its isomeric forms, or a carboxyalkanoyl group of 1 to 6 carbons, such as an oxalyl, malonyl, succinyl, glutaryl group, or a aromatic acyl group such as benzoyl, or a halo, nitro or alkyl substituted benzoyl group. The word 'alkyl' as used in the description or the claims, denotes a straight-chain or branched alkyl radical of 1 to 10 carbons, in all its isomeric forms. Alkoxyalkyl protecting groups are groupings such a methoxymethyl, ethoxyethyl, methoxyethoxymethyl, or tetrahydrofuranyl and tetrahydropyranyl. Preferred alkylsilyl-protecting groups are trimethylsilyl, triethylsilyl, t-butyldimethylsilyl, and analogous alkylated silyl radicals.

The vitamin D compounds useful in the present treatment are either 24,28-methylene-1α,25-dihydroxyvitamin $D_2$ or 24,28-methylene-1α-hydroxyvitamin $D_2$. The above compounds may be administered alone or in combination with other pharmaceutically acceptable agents.

The vitamin D compounds or combinations thereof can be readily administered as sterile parenteral solutions by injection or intravenously, or by alimentary canal in the form of oral dosages, or trans-dermally, or by suppository. Doses of from about 0.5 micrograms to about 50 micrograms per day of 24,28-methylene-1α,25-dihydroxyvitamin $D_2$ or 24,28-methylene-1α-hydroxyvitamin $D_2$ compound per se, or in combination with other 1α-hydroxylated vitamin D compounds, the proportions of each of the compounds in the combination being dependent upon the particular disease state being addressed and the degree of bone mineralization and/or bone mobilization desired, are generally effective to practice the present invention. In all cases sufficient amounts of the compound should be used to restore bone mass. Amounts in excess of about 50 micrograms per day or the combination of that compound with other 1α-hydroxylated vitamin D compounds, are generally unnecessary to achieve the desired results, may result in hypercalcemia, and may not be an economically sound practice. In practice the higher doses are used where therapeutic treatment of a disease state is the desired end while the lower doses are generally used for prophylactic purposes, it being understood that the specific dosage administered in any given case will be adjusted in accordance with the specific compounds being administered, the disease to be treated, the condition of the subject and the other relevant medical facts that may modify the activity of the drug or the response of the subject, as is well known by those skilled in the art. For example, to be effective, either 24,28-methylene-1α,25-dihydroxyvitamin $D_2$ or 24,28-methylene-1α-hydroxyvitamin $D_2$ is preferably administered in a dosage range of 0.5-50 μg/day. In general, either a single daily dose or divided daily dosages may be employed, as is well known in the art.

Dosage forms of the various compounds can be prepared by combining them with non-toxic pharmaceutically acceptable carriers to make either immediate release or slow release formulations, as is well known in the art. Such carriers may be either solid or liquid such as, for example, corn starch, lactose, sucrose, peanut oil, olive oil, sesame oil and propylene glycol. If a solid carrier is used the dosage form of the compounds may be tablets, capsules, powders, troches or lozenges. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances.

The present invention is more specifically described by the following examples, which are meant to be illustrative only of the process of synthesis and of the novel compounds, both end products and intermediates, obtainable thereby. In these examples, specific compounds identified by Arabic numerals (e.g. compounds 1, 2, 3, . . . etc.) refer to the structures so numbered in the process schematics. Additionally examples are provided which are illustrative of the distinctive biological characteristics of the new compounds, such characteristics serving as a basis for the application of these compounds in the treatment of metabolic bone disease.

PREPARATION OF COMPOUNDS

General Procedures

Ultraviolet (UV) absorption spectra were recorded with a Perkin-Elmer Lambda 3B uv-vis spectrophotometer. Proton nuclear magnetic resonance ($^1$H-NMR) spectra were recorded at 400 MHz with a Bruker AM-400 widebore multinuclear spectrometer or at 500 MHz with a Bruker AM-500 multinuclear spectrometer in chloroform-d (CDCl$_3$). Chemical shifts (δ) are reported downfield from internal tetramethylsilane (TMS: δ0.00) or chloroform (δ7.24). High-resolution mass spectra (HRMS) were recorded at 70 eV on a Kratos MS-50 TC instrument equipped with a Kratos DS-55 Data System. High-resolution data were obtained by peak matching. Samples were introduced into the ion source maintained at 120°-250° C. via a direct-insertion probe. Silica gel 60 (Merck, 230-400 mesh) was used for column chromatography. High performance liquid chromatography (HPLC) was performed using a Waters Associates Liquid chromatography equipped with a Model 6000A solvent delivery system, a Model U6K injector and a Model 450 variable wavelength detector. Tetrahydrofuran was distilled from sodium-benzophenone ketyl under nitrogen. Other solvents were purified by standard methods.

EXAMPLES

In Process Schemes I and II the following abbreviations are employed:

| | |
|---|---|
| DMF: | N,N-dimethylformamide |
| Ac: | acetyl |
| Et: | ethyl |
| DMSO: | dimethylsulfoxide |
| Ts: | p-toluenesulfonyl |
| DMAP: | N,N-dimethyl-4-aminopyridine |
| Ph: | phenyl |
| PPTS: | pyridinium p-toluenesulfonate |
| Me: | methyl |
| mCPBA: | 3-chloroperbenzoic acid |
| TES: | triethylsilyl |
| Bu: | butyl |

It should be noted that in the present description and in schemes I and II, compound 11 is a known compound and may be prepared in accordance with PCT Patent Application No. WO88/07545.

EXAMPLE 1

Synthesis of 24,28-Methylene-1α,25-Dihydroxyvitamin $D_2$ (compound 13; Process Scheme I)

The synthesis of compound 13 may be summarized as follows:

The synthesis of the side chain sulfone 9 started with bis-alkylation of ethyl acetoacetate. Ethyl acetoacetate was treated with 1,2-dibromoethane in the presence of potassium hydroxide in dimethylsulfoxide to yield cyclopropane ketoester 1. After protection of the ketone as a ketal, the ester was reduced with lithium aluminum hydride to alcohol 3. The alcohol 3 was converted via the corresponding tosylate 4, into phenyl sulfide 5. Deprotection of the ketal and alkylation of the regenerated ketone with methyl Grignard reagent gave tertiary alcohol 7. The sulfide was oxidized with peracid to sulfone 8 and the hydroxy group was protected as a silyl ether to give a protected sulfone 9.

The sulfone 9 was de-protonated with a base and then condensed with an aldehyde 11. The resulting hydroxy sulfone was acetylated and then was submitted to reductive elimination with sodium-amalgam to give an (E)-olefin. The 1α- and 3β-hydroxy groups of which protective groups had been removed during the reductive elimination were re-protected to give 10. Deprotection of 3β- and 25-hydroxy groups yielded provitamin 12. Photo- and thermoisomerization, followed by deprotection of 1α-hydroxy group, gave compound 13.

Ethyl 1-acetylcyclopropanecarboxylate 1

A mixture of ethyl acetoacetate (13.0 g, 99.9 mmol), 1,2-dibromoethane (13 mL, 151 mmol) and potassium hydroxide (14.0 g, 250 mmol) in dimethylsulfoxide (130 mL) was stirred at ambient temperature overnight. The mixture was poured into ice water and extracted with diethyl ether. The combined organic layers were washed with brine, and dried over sodium sulfate. Filtration and concentration gave 16.22 g of an oily material, which was purified by column chromatography (silica gel 80 g, 20% ethyl acetate in n-hexane) to give 12.97 g (83.1%) of 1, as a pale yellow oil.

$^1$H-NMR (CDCl$_3$, 500 MHz) δ: 1.21 (3H, t, J=7.2 Hz), 1.38(4H, s), 2.39(3H, s), 4.13(2H, q, J=7.2 Hz)

Ethyl 1-(2-methyl-1,3-dixolan-2-yl)cyclopropanecarboxylate 2

A mixture of 1 (12.97 g, 83.0 mmol), ethylene glycol (23 mL, 412 mmol), triethyl orthoformate (28 mL, 168 mmol) and p-toluenesulfonic acid monohydrate (1.58 g, 8.31 mmol) in toluene (100 mL) was heated at 80°-90° C. with stirring for 1 hr. The mixture was cooled to ambient temperature and poured into cold sodium bicarbonate solution. The organic layer was separated, and the aqueous layer was extracted with diethyl ether. The combined organic layers were washed with sodium bicarbonate solution and brine, and dried over sodium sulfate. Filtration and concentration gave 21.43 g of an oily material, which was purified by column chromatography (silica gel 80 g, 20% ethyl acetate in n-hexane) to give 16.07 g (96.7%) of 2, as colorless oil.

$^1$H-NMR (CDCl$_3$, 500 MHz) δ: 0.91(2H, m) 1.05(2H, m) 1.14(3H, t, J=7.3 Hz), 1.51(3H, s), 3.79(2H, m), 3.85(2H, m), 4.03(2H, q, J=7.3 Hz)

1-Hydroxymethyl-1-(2-methyl-1,3-dioxolan-2-yl)cyclopropane 3

To a stirred and ice-cooled suspension of lithium aluminum hydride (3.83 g, 101 mmol) in diethyl ether (500 mL) was added a solution of 2 (16.07 g, 80.3 mmol) in diethyl ether (200 mL) dropwise over 80 min under nitrogen. The mixture was stirred for 15 min. To the mixture were added water (3.83 mL), 15% sodium hydroxide solution (11.5 mL) and water (11.5 mL), followed by an addition of sodium sulfate (49 g). The mixture was filtered through a pad of Celite and the precipitate was washed with diethyl ether thoroughly. The combined organic solution was concentrated to give 12.25 g of an oily material, which was purified by column chromatography (silica gel 60 g, 50% ethyl acetate in n-hexane) to give 11.81 g (93.0%) of 3, as a colorless oil.

$^1$H-NMR (CDCl$_3$, 500 MHz) δ: 0.42(2H), 0.68(2H), 1.39(3H, s), 2.92(1H, t, J=5.8 Hz), 3.51(2H, d, J=5.8 Hz), 3.93(4H, br s)

1-(2-Methyl-1,3-dioxolan-2-yl)-1-p-toluenesulfonyloxymethylcyclopropane 4.

To a stirred and ice-cooled solution of 3 (5.0 g, 31.6 mmol), N,N-dimethyl-4-aminopyridine (386 mg, 8.16 mmol) and triethylamine (22 mL, 158 mmol) in dichloromethane (25 mL) was added p-toluenesulfonyl chloride (7.23 g, 37.9 mmol) portionwise and the mixture was stirred in a cold room at 4° C. overnight. The mixture was poured into ice water, and the organic layer was separated. The aqueous layer was extracted with diethyl ether. The combined organic layers were washed with water and brine, and dried over sodium sulfate. Filtration and concentration gave 16.70 g of crude 4, as a pale yellow oil, which was used in the next step without further purification.

1-(Benzenesulfenylmethyl)-1-(2-methyl-1,3-dioxolan-2-yl)cyclopropane 5

To a mixture of crude 4 (prepared above, 16.70 g) and triethylamine (8.8 mL, 63.1 mmol) in N,N-dimethylformamide (30 mL) was added thiophenol (5.0 mL, 48.7 mmol) in one portion. The mixture was stirred at 0°-5° C. for 1 hr and then at ambient temperature for 1.5 hr. The mixture was poured into cold brine, and extracted with diethyl ether and n-hexane. The combined organic layers were washed with water and brine, and dried over sodium sulfate. Filtration and concentration gave 9.85 g of an oily material, which was purified by column chromatography (silica gel 50 g, 4-12% ethyl acetate in n-hexane) to give 7.64 g (96.6% form 3) of 5, as a pale yellow oil.

$^1$H-NMR (CDCl$_3$, 400 MHz) δ: 0.57(2H, m), 0.74(2H, m), 1.45(3H, s), 3.23(2H, s), 3.97(4H, s), 7.13(1H, t, J=6.9 Hz), 7.20-7.35(4H)

1-Acetyl-1-(benzenesulfenylmethyl)cyclopropane 6

A mixture of 5 (7.23 g, 2.94 mmol) and pyridinium p-toluenesulfonate (0.74 g, 2.94 mmol) in acetone (150 mL) was stirred in a cold room at 4° C. for 5 days. The mixture was neutralized with sodium bicarbonate solution, and diluted with toluene. After evaporation of acetone, the residue was diluted with water and extracted with ethyl acetate. The combined organic layers were washed with brine, and dried over sodium sulfate. Filtration and concentration gave 9.22 g of an oily material, which was purified by column chromatography (silica gel 60 g, 4-16% ethyl acetate in n-hexane) to give 6.16 g (quantitative) of 6, as a pale yellow oil.

$^1$H-NMR (CDCl$_3$, 500 MHz) δ: 0.93(2H, s), 1.28(2H, s), 2.12(3H, s), 3.26(2H, s), 7.17(1H), 7.24(2H), 7.33(2H)

1-Benzenesulfenylmethyl-1-(2-hydroxy-2-propyl)cyclopropane 7

To a stirred and ice-cooled solution of 6 (6.16 g, 29.9 mmol) in diethyl ether (60 mL) was added a solution of methylmagnesium bromide (3.0M solution in diethyl ether, 12 mL) dropwise over 10 min under nitrogen. The mixture was stirred for 20 min. The reaction was quenched by an addition of ammonium chloride solution and the organic layer was separated. The aqueous layer was extracted with diethyl ether and the combined organic layers were washed with brine, and dried over sodium sulfate. Filtration and concentration gave 5.80 g of an oily material, which was purified by column chromatography (silica gel 60 g, 4-10% ethyl acetate in n-hexane) to give 4.83 g (71.2%) of 7, as a colorless oil.

$^1$H-NMR (CDCl$_3$, 500 MHz) δ: 0.51(2H, br s), 0.69(2H, br s), 1.27(6H, br s), 3.17(2H, s), 7.16(1H), 7.26(2H), 7.33(2H)

1-Benzenesulfonylmethyl-1-(2-hydroxy-2-propyl)cyclopropane 8

To a solution of 7 (4.83 g, 21.3 mmol) in dichloromethane (50 mL) was added sodium bicarbonate (10.1 g, 120 mmol) and water (65 mL) and the mixture was stirred vigorously in an ice bath. To the mixture was added m-chloroperbenzoic acid (ca. 85%, 10.4 g, 51.2 mmol) portionwise and the mixture was stirred for 20 min. The excess amount of peracid was decomposed with sodium thiosulfate solution in the presence of potassium iodide. The organic layer was separated and the aqueous layer was extracted with ethyl acetate. The combined organic layers were washed with brine, and dried over sodium sulfate. Filtration and concentration gave 6.30 g of an oily material, which was purified by column chromatography (silica gel 50 g, 5-33% ethyl acetate in n-hexane) to give 4.05 g (74.8%) of 8, as a colorless oil.

$^1$H-NMR (CDCl$_3$, 500 MHz) δ: 0.70(2H, dd, J=6.6 and 5.4 Hz), 0.80(2H, dd, J=6.6 and 5.4 Hz), 1.14(6H, s), 3.36(2H, s), 7.55(2H, t, J=7.4 Hz), 7.64(1H, t, J=7.4 Hz), 7.91(2H, d, J=7.4 Hz)

1-Benzenesulfonylmethyl-1-(2-triethylsilyloxy-2-propyl)cyclopropane 9

To a stirred and ice-cooled solution of 8 (4.05 g, 15.9 mmol) and imidazole (2.16 g, 31.7 mmol) in N,N-dimethylformamide was added chlorotriethylsilane (4 mL, 23.8 mmol), and the mixtrue was stirred at ambient temperature overnight. To the mixture was added ice and diethyl ether and the mixture was stirred at ambient temperature for 20 min. The organic layer was separated and the aqueous layer was extracted with diethyl ether. The combined organic layers were washed with brine, and dried over sodium sulfate. Filtration and concentration gave 7.40 g of an oily material, which was purified by column chromatography (silica gel 70 g, 4-12% ethyl acetate in n-hexane) to give 5.89 g (quantitative) of 9, as a colorless oil. $^1$H-NMR (CDCl$_3$, 500 MHz) δ: 0.55 (6H, q, J=7.9 Hz), 0.80(2H, dd, J=6.8 and 4.2 Hz), 0.91(9H, t, J=7.9 Hz), 0.92(2H), 1.20 (6H, s), 3.39(2H, s), 7.55(2H, t, J=7.4 Hz), 7.64(1H, t, J=7.4 Hz), 7.89(2H, d, J=7.4 Hz)

(22E)-24,28-Methylene-1α,3β-bis(methoxycarbonyloxy)-25-triethylsilyloxyergosta-5,7,22-triene 10

To a stirred solution of 9 (1.20 g, 3.26 mmol) in tetrahydrofuran (25 mL) was added a solution of lithium diethylamide (prepared from 1.32 mL of diethylamine and 7.6 mL of 1.6N n-butyllithium in 21 mL of tetrahydrofuran; 8.3 mL) dropwise at −50°-60° C. under nitrogen. The mixture was stirred at the same temperature for 35 min then cooled to −78° C. (dry ice-methanol bath). To the mixture was added a solution of (20S)-1α,3β-bis(methoxycarbonyloxy)-20-methylpregna-5,7-dien-21-al 11 (1.0 g, 2.17 mmol) in tetrahydrofuran (30 mL) dropwise over 2 hr. The mixture was stirred for 1 hr and then quenched by an addition of ammonium chloride solution and ethyl acetate. The organic layer was separated, and aqueous layer was extracted with ethyl acetate. The combined organic layers were washed with brine, and dried over sodium sulfate. Filtration and concentration gave 3.65 g of an oily residue, which was used directly in the next reaction. The residue (3.65 g) was dissolved in dichloromethane (30 mL) and was treated with acetic anhydride (2 mL) in the presence of N,N-dimethyl-4-aminopyridine (3.17 g) at ambient temperature overnight. To the mixture was added ice and the mixture was stirred at ambient temperature for 30 min. The organic layer was separated and the aqueous layer was extracted with ethyl acetate. The combined organic layers were washed with water, sodium bicarbonate solution and brine, and dried over sodium sulfate. Filtration and evaporation gave 3.69 g of an oily residue, which was used directly in the next reaction. The residue (3.69 g) was dissolved in a mixtrue of tetrahydrofuran (50 mL) and methanol (50 mL) and the solution was cooled at −20°-30° C. To the stirred and cooled solution was added sodium bicarbonate (3.4 g) and 5% sodium amalgam (pulverized and washed with tetrahydrofuran, 19 g). The mixture was stirred at the same temperature for 4 hr, and then was allowed to warm to ambient temperature. After stirred overnight, the supernatant was filtered through a pad of Celite, and the precipitate was washed with ethyl acetate. The combined organic solution was poured into water. The organic layer was separated, and the aqueous layer was extracted with ethyl acetate. The combined organic layers were washed with brine, and dried over sodium sulfate. Filtration and concentration gave 2.89 g of a residue, to which was added dimethyl carbonate (100 mL) and sodium methoxide (a catalytic amount). The mixture was heated under reflux for 4 hr with the formed methanol removed by passing through a pad of molecular sieves 4A. The mixture was cooled and poured into ice water. The organic layer was separated, and the aqueous layer was extracted with ethyl acetate. The combined organic layers were washed with brine, and dried over sodium sulfate. Filtration and concentration gave 2.72 g of a residue which was purified by column chromatography (silica gel 20 g, 2.5-20% ethyl acetate in n-hexane) to give 680 mg (46.7% from 11) of 10, as white solids.

$^1$H-NMR (CDCl$_3$, 500 MHz) δ: 3.77(3H, s), 3.79(3H, s), 4.84(1H, m), 4.90(1H, m), 5.12(1H, dd, J=15.2 and 8.9 Hz), 5.37(1H, m), 5.65(1H, d, J=15.2 Hz), 5.68(1H, m)

(22E)-24,28-Methylene-1α-methoxycarbonyloxyergosta-5,7,22-triene-3β, 25-diol 12

To a solution of 10 (566 mg, 0.844 mmol) in tetrahydrofuran (10 mL) was added 1.0M solution of tetra-n-butylammonium fluoride in tetrahydrofuran (3.4 mL, 3.4 mmol) and the mixture was stirred at ambient temperature for 5.5 hr. The mixture was poured into ice water, and extracted with ethyl acetate. The combined organic layers were washed with sodium bicarbonate solution and brine, and dried over sodium sulfate. Filtration and concentration gave 1.41 g of a residue. To the residue was added methanol (30 mL) and 1N lithium hydroxide solution (3 mL), and the mixture was stirred at ambient temperature overnight. To the mixture was added methanol (20 mL) and the mixture was stirred at ambient temperature for 1 day. To the mixture was added methanol (50 mL) and 1N lithium hydroxide solution (5 mL) and the mixture was stirred for 4 hr. The mixture was neutralized with 1N hydrochloric acid, and the methanol was evaporated under reduced pressure. The residue was diluted with water and extracted with ethyl acetate. The combined organic layers were washed with sodium bicarbonate solution and brine, and dried over sodium sulfate. Filtration and concentration gave 0.70 g of a residue, which was purified by column chromatography (silica gel 20 g, 10-80% ethyl acetate in n-hexane) to give 283 mg (67.2%) of 12, as white solids.

$^1$H-NMR (CDCl$_3$, 500 MHz) δ: 0.44(1H, d, J=10.1 Hz), 0.45(1H, d, J=10.1 Hz), 0.62(3H, s), 0.71(2H, br s), 1.00(3H, d, J=6.7 Hz), 1.00(3H, s), 1.21(6H, s), 3.78(3H, s), 3.99(1H, m), 4.82(1H, br s), 5.28(1H, dd, J=15.2 and 9.0 Hz), 5.37(1H, m), 5.66(1H, m), 5.73(1H, d, J=15.2 Hz)

(5Z,7E,22E)-24,28-Methylene-9,10-secoergosta-5,7,10(19), 22-tetraene-1α,3β,25-triol 13

A solution of 12 (104 mg, 0.209 mmol) in diethyl ether (100 mL) and benzene (20 mL) was irradiated with medium pressure mercury lamp for 30 min through a Vycor filter in an ice bath under nitrogen. The mixture was concentrated under reduced pressure, and the residue was dissolved in benzene (50 mL). The solution was heated under reflux for 30 min, and then left to stand at ambient temperature under nitrogen for 8 days. The mixture was concentrated under reduced pressure, and the residue was treated with 1N lithium hydroxide solution (1 mL) in methanol (9 mL) at ambient temperature for 1.5 hr under nitrogen. The mixture was poured into ice water and extracted with ethyl acetate. The combined organic layers were washed with brine, and dried over sodium sulfate. Filtration and concentration gave a residue, which was purified by column chromatography (silica gel 5 g, 33–80% ethyl acetate in n-hexane) and high performance liquid chromatography [Zorbax Pro-10 SIL (Mitsui Toatsu) 20 mm$\phi$×250 mm, 80% ethyl acetate in n-hexane] to give 21.0 mg (22.8%) of 13, as a colorless viscous oil.

HRMS m/z: Found 440.3315; Calcd for $C_{29}H_{44}O_3$ 440.3290

UV (EtOH): $\lambda_{max}$ 264 nm, $\lambda_{min}$ 227 nm $^1$H-NMR (CDCl$_3$, 400 MHz) $\delta$: 0.45(2H), 0.55(2H, br s), 0.71(3H, s), 0.99(3H, d, J=6.2 Hz), 1.21(6H, s), 4.23(1H, m), 4.43(1H, m), 4.99(1H, br s), 5.29(1H, dd, J=15.1 and 9.2 Hz), 5.32(1H, br s), 5.72(1H, d, J=15.1 Hz), 6.01(1H, d, J=11.4 Hz), 6.37(1H, d, J=11.4 Hz)

EXAMPLE 2

Synthesis of 24,28-Methylene-1α-hydroxyvitamin D$_2$ (compound 19; Process Scheme II)

The synthesis of compound 19 may be summarized as follows:

The keto sulfide 6 was homologated by Wittig reaction using methoxymethylenephosphorane, followed by acidic hydrolysis of resulting enol ether, to yield aldehyde 14. The formyl group of 14 was converted into a methyl group by a modified Wolff-Kishner reduction to yield sulfide 15. The sulfide 15 was oxidized with a peracid to sulfone 16. The sulfone 16 was condensed with aldehyde 11, and then converted into 17 in the same manner as for the conversion of sulfone 9 into 10 in Example 1. The protective group of 3β-hydroxy group of 17 was removed to yield provitamin 18. Photo- and thermoisomerization of 18, followed by deprotection of 1α-hydroxy group, yielded compound 19.

2-(1-Benzenesulfenylmethylcyclopropan-1-yl)propanal 14

To a stirred and ice-cooled suspension of methoxymethyltriphenyl phosphonium chloride (5.72 g, 16.7 mmol) in diethyl ether (60 mL) was added n-butyllithium (1.6N solution in n-hexane, 10.4 mL, 16.6 mmol) dropwise under nitrogen. The mixture was stirred for 30 min, then was cooled to −40° C. To the mixture was added a solution of 6 (2.86 g, 13.9 mmol) in diethyl ether (15 mL) dropwise over a period of 1.5 hr. The mixture was allowed to warm to ambient temperature and was stirred overnight. The mixture was diluted with n-hexane and filtered through a pad of Celite, and the precipitate was washed with 30% diethyl ether in n-hexane. The combined organic solution was concentrated to give 4.36 g of an oily material, which was dissolved in tetrahydrofuran (40 mL). To the mixture was added 1N hydrochloric acid (10 mL) and the mixture was stirred at ambient temperature for 4 hr. and then heated under reflux for 80 min. The mixture was cooled and poured into ice water, and extracted with diethyl ether. The combined organic layers were washed with sodium bicarbonate solution and brine, and dried over sodium sulfate. Filtration and concentration gave 7.39 g of an oily material, which was purified by column chromatography (silica gel 30 g, 5–15% ethyl acetate in n-hexane) to give 2.14 g (69.8%) of 14, as a colorless oil.

$^1$H-NMR (CDCl$_3$, 500 MHz) $\delta$: 0.50(1H, m), 0.58(1H, m), 0.64(1H, m), 0.70(1H, m), 1.13(3H, d, J=7.0 Hz), 2.03(1H, q, J=7.0 Hz), 2.78(1H, d, J=14.0 Hz), 3.19(1H, d, J=14.0 Hz), 7.10–7.40(5H), 9.90(1H, s)

1-Benzenesulfenylmethyl-1-(2-propyl)cyclopropane 15

A mixture of 14 (2.12 g, 8.62 mmol), hydrazine hydrate (55% in water, 7.4 mL, 131 mmol) and potassium carbonate (3.2 g, 23.2 mmol) in diethylene glycol (21 mL) was heated at 150° C. (bath temperature) for 3 hr. After cooled to ambient temperature, the mixture was poured into ice water and extracted with n-hexane. The combined organic layers were washed with cold diluted hydrochloric acid, water, sodium bicarbonate solution and brine, and dried over sodium sulfate. Filtration and concentration gave 1.81 g of an oily material, which was purified by column chromatography (silica gel 20 g, 1–2% ethyl acetate in n-hexane) to give 1.69 g (85.1%) of 15, as a colorless oil.

$^1$H-NMR (CDCl$_3$, 500 MHz) $\delta$: 0.41(2H, m), 0.45(2H, m), 0.95(6H, d, J=6.8 Hz), 1.59(1H, sept, J=6.8 Hz), 3.02(2H, s), 7.10–7.32(5H)

1-Benzenesulfonylmethyl-1-(2-propyl) cyclopropane 16

To a stirred and ice-cooled mixture of 15 (1.69 g, 8.19 mmol) in dichloromethane (17 mL) and saturated sodium bicarbonate solution (17 mL) was added m-chloroperbenzoic acid (85%, 3.66 g, 18.0 mmol) portionwise. The mixture was stirred at ambient temperature for 30 min. After decomposition of an excess amount peracid with sodium thiosulfate solution in the presence of potassium iodide, the organic layer was separated, and the aqueous layer was extracted with diethyl ether. The combined organic layers were washed with sodium bicarbonate solution and brine, and dried over sodium sulfate. Filtration and concentration gave 2.41 g of an oily material, which was purified by column chromatography (silica gel 25 g, 10% ethyl acetate in n-hexane) to give 1.74 g (89.1%) of 16, as a colorless oil.

$^1$H-NMR (CDCl$_3$, 500 MHz) $\delta$: 0.38(2H, m), 0.51(2H, m), 0.80(6H, d, J=6.8 Hz), 2.07(1H, sept, J=6.8 Hz), 3.12(2H, s), 7.56(2H, t, J=7.7 Hz), 7.65(1H, t, J=7.7 Hz), 7.91(2H, d, J=7.7 Hz)

(22E)-24,28-Methylene-1α,3β-bis(methoxycarbonyloxy)ergosta-5,7,22-triene 17

To a stirred solution of 16 (0.78 g, 3.27 mmol) in tetrahydrofuran (25 mL) was added a solution of lithium diethylamide (prepared from 1.32 mL of diethylamine and 7.6 mL of 1.6N solution of n-butyllithium in n-hexane in 21 mL of tetrahydrofuran; 8.3 mL) dropwise at −50°—−60° C. under nitrogen. The mixture was stirred at −50°—−60° C. for 30 min and was cooled to −78° C. (dry ice-methanol bath). To the mixture was added a solution of 11 (1.0 g, 2.17 mmol) in tetrahydrofuran (30 mL) dropwise over a period of 110 min. After stirred for 45 min, the mixture was quenched by an addition of ammonium chloride solution and ethyl acetate. The organic layer was separated, and the aqueous layer was extracted with ethyl acetate. The combined organic layers were washed with brine, and dried over sodium sulfate. Filtration and concentration gave 3.23 g of an oily material, which was dissolved in dichloromethane (30 mL). To the solution N,N-dimethyl-4-aminopyridine (3.17 g) and acetic anhydride (2 mL) was added, and the mixture was stirred at ambient temperature overnight. To the mixture ice was added, and the mixture was stirred for 30 min at ambient temperature. The organic layer was separated, and the aqueous layer was extracted with ethyl acetate. The combined organic layers were washed with water, sodium bicarbonate solution and brine, and dried over sodium sulfate. Filtration and concentration gave 3.45 g of an oily material, which was dissolved in a mixture of tetrahydrofuran (50 mL) and methanol (50 mL) and cooled in a dry ice-carbon tetrachloride bath. To the mixture was added sodium bicarbonate (3.41 g), followed by sodium amalgam (5%, pulverized and washed with tetrahydrofuran just prior to use, 19 g), the mixture was stirred for 3.5 hr then allowed to warm to ambient temperature and stirred overnight. The supernatant was filtered through a pad of Celite and the precipitate was washed with ethyl acetate. The combined organic solution was poured into water and extracted with ethyl acetate. The combined organic layers were washed with brine, and dried over sodium sulfate. Filtration and concentration gave 2.75 g of a residue, to which dimethyl carbonate (100 mL) and a catalytic amount of sodium methoxide were added. The mixture was heated under reflux, with removal of methanol formed with molecular sieves 4A, for 2 hr. After cooled to ambient temperature, the mixture was poured into ice water, and extracted with ethyl acetate. The combined organic layers were washed with brine, and dried over sodium sulfate. Filtration and concentration gave 4.44 g of a residue, which was purified by column chromatography (silica gel 20 g, 10–20% ethyl acetate in n-hexane) to give 574 mg (48.9% from 11) of 17, as white solids.

$^1$H-NMR (CDCl$_3$, 500 MHz) δ: 0.34(2H, br s), 0.46(2H, m), 0.62(3H, s), 0.91(6H, d, J=6.5 Hz), 0.99(3H, d, J=6.6 Hz), 1.01(3H, s), 3.77(3H, s), 3.99(3H, s), 4.84(1H, br s), 4.90(1H, m), 5.51(1H, dd, J=15.2 Hz and 8.8 Hz), 5.37(1H, m), 5.52(1H, d, J=15.2 Hz), 5.68(1H, m)

(22E)-24,28-Methylene-1α-methoxycarbonyloxyergosta-5,7,22-trien-3β-ol 18

A mixture of 17 (544 mg, 1.01 mmol) and lithium hydroxide monohydrate (0.1 g) in a mixture of methanol (10 mL) and diethyl ether (40 mL) was stirred at ambient temperature for 5.25 hr. The mixture was neutralized with 1N hydrochloric acid and the solvent was evaporated under reduced pressure. The residue was diluted with water and extracted with ethyl acetate. The combined organic layers were washed with sodium bicarbonate solution and brine, and dried over sodium sulfate. Filtration and concentration gave 1.02 g of a residue, which was purified by column chromatography (silica gel 15 g, 20–80% ethyl acetate in n-hexane) to give 287 mg (58.9%) of 18, as white solids $^1$H-NMR (CDCl$_3$, 500 MHz)δ: 0.37(2H, br s), 0.48(2H, m), 0.64(3H, s) 0.94(6H, d, J=6.5 Hz), 1.02(3H, d, J=6.6 Hz), 1.03(3H, s), 3.81(3H, s), 4.02(1H, m), 4.85(1H, br s), 5.17(1H, dd, J=15.2 and 8.8 Hz), 5.39(1H, m), 5.54(1H, d, J=15.2 Hz), 5.70(1H, m)

(5Z,7E,22E)-24,28-Methylene-9,10-secoergosta-5,7,10(19),22-tetraene-1α,3β-diol 19

An ice-cooled and stirred solution of 18 (104 mg, 0.215 mmol) in a mixture of benzene (20 mL) and diethyl ether (100 mL) was irradiated with a medium pressure mercury lamp through a Vycor filter for 30 min under nitrogen. The mixture was concentrated under reduced pressure and the residue was dissolved in benzene (50 mL). The solution was heated under reflux for 30 min and then left to stand at ambient temperature for 8 days under nitrogen. The solvent was evaporated under reduced pressure, and to the residue were added 1N lithium hydroxide solution (1 mL) and methanol (9 mL). The mixture was stirred at ambient temperature for 2.5 hr under nitrogen. The mixture was poured into ice water, and was extracted with ethyl acetate. The combined organic layers were washed with brine, and dried over sodium sulfate. Filtration and concentration gave a residue, which was purified by column chromatography (silica gel 5 g, 35–65% ethyl acetate in n-hexane) and then high performance liquid chromatography [Zorbax Pro-10 SIL (Mitsuit Toatsu) 20 mmφ±250 mm, 75% ethyl acetate in n-hexane] to give 20.8 mg (22.8%) of 19, as white solids.

HRMS m/z: Found 424.3350; Calcd for C$_{29}$H$_{44}$O$_2$ 424.3341

UV (EtOH): λ$_{max}$ 264 nm, λ$_{min}$ 226 nm $^1$H-NMR (CDCl$_3$, 400 MHz)δ: 0.35(2H, br s), 0.46(2H, m), 0.55(3H, s), 0.92(6H, d, J=6.6 Hz), 0.99(3H, d, J=6.9 Hz), 4.23(1H, m), 4.43(1H, m), 5.00(1H, br s), 5.15(1H, dd, J=15.2 and 8.8 Hz), 5.33(1H, br s), 5.51(1H, d, J=15.2 Hz), 6.02(1H, d, J=11.4 Hz), 6.38(1H, d, J=11.4 Hz)

BIOLOGICAL ACTIVITY OF CYCLOPROPANE DERIVATIVES: PROCEDURE

Male weanling rats were obtained from the Holtzman strain of the Sprague-Dawley Company and were placed on a purified 0.2% calcium/0.3% phosphorus diet for three weeks and then were provided the indicated compounds intraperitoneally in 95% propylene glycol/5% ethanol (0.1 ml) each day for 7 days. The rats were killed 23-24 hours after the last dose. The values are expressed as the mean±S.E.M. Intestinal calcium transport was measured by the everted sac technique described by Martin and DeLuca [Am. J. Physiol. 212:1351–1359 (1969)]. Serum calcium was measured using the Calcette Automatic Calcium Titractor (Precision Systems, Inc., Natick. Mass.).

INTERPRETATION

The results demonstrate that the cyclopropane derivative of 1α,25-dihydroxyvitamin D$_2$ (Compound III) has activity on intestinal calcium transport equal to or similar to that exhibited by the native hormone, 1α,25-dihydroxyvitamin D$_3$. Similarly, the cyclopropane derivative of 1α-hydroxyvitamin D$_2$ (Compound IV) is fully effective in inducing intestinal calcium transport similar to that of the native hormone. Unlike the native hormone, however, compound IV had no measurable activity at the dose levels provided of inducing the mobilization of calcium from bone. Compound III, however, did show slight activity at the higher dose level, i.e. 195 pmol/day for 7 days, but its activity in this regard is below that of the native hormone.

These results suggest that because of the lack of bone calcium mobilization activity and the full activity in intestinal calcium transport, these compounds are attractive for the treatment of diseases wherein bone loss is the underlying factor. Such diseases are postmenopausal osteoporosis, steroid-induced osteoporosis, and osteoporosis of the elderly.

| Group | Dose (pmol/day/7 d) | Intestinal Calcium Transport (S/M) | Serum Calcium (mg/dl) |
|---|---|---|---|
| —D | 0 | 3.6 ± 0.1 | 4.4 ± 0.1 |
| 1,25-(OH)$_2$D$_3$ | 195 | 7.6 ± 0.4 | 6.2 ± 0.4 |

BONE CALCIUM MOBILIZATION (SERUM CALCIUM) AND INTESTINAL CALCIUM TRANSPORT ACTIVITY OF 24,28-METHYLENE-1α,25-(OH)$_2$D$_2$ (III) AND 24,28-METHYLENE-1α-OH-D$_2$ (IV)

-continued

BONE CALCIUM MOBILIZATION (SERUM CALCIUM) AND INTESTINAL CALCIUM TRANSPORT ACTIVITY OF 24,28-METHYLENE-1α,25-(OH)$_2$D$_2$ (III) AND 24,28-METHYLENE-1α-OH-D$_2$ (IV)

| Group | Dose (pmol/day/7 d) | Intestinal Calcium Transport (S/M) | Serum Calcium (mg/dl) |
|---|---|---|---|
| III | 65 | 5.3 ± 0.3 | 4.6 ± 0.1 |
|  | 195 | 5.9 ± 0.7 | 5.0 ± 0.1 |
| IV | 65 | 6.6 ± 0.4 | 4.6 ± 0.1 |
|  | 195 | 6.8 ± 0.4 | 4.3 ± 0.1 |

Because these compounds are approximately equal in intestinal calcium transport activity as 1,25-(OH)$_2$D$_3$ but are very much less active in mobilizing bone calcium, they would appear to be ideal for treatment of diseases where bone formation is desired.

For treatment purposes, the novel compounds of this invention may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds may be administered orally, parenterally or transdermally. The compounds are advantageously administered by injection or by intravenous infusion of suitable sterile solutions, or in the form of liquid or solid doses via the alimentary canal, or in the form of creams, ointments, patches, or similar vehicles suitable for transdermal applications. Doses of from 0.5 μg to 50 μg per day of the compounds are appropriate for treatment purposes, such doses being adjusted according to the disease to be treated, its severity and the response of the subject as is well understood in the art. Since the new compounds exhibit specificity of action, each may be suitably administered alone, in situations where only calcium transport stimulation is desired, or together with graded doses of another active vitamin D compound—e.g. 1α-hydroxyvitamin D$_2$ or D$_3$, or 1α,25-dihydroxyvitamin D$_3$—in situations where some degree of bone mineral mobilization (together with calcium transport stimulation) is found to be advantageous.

PROCESS SCHEME I

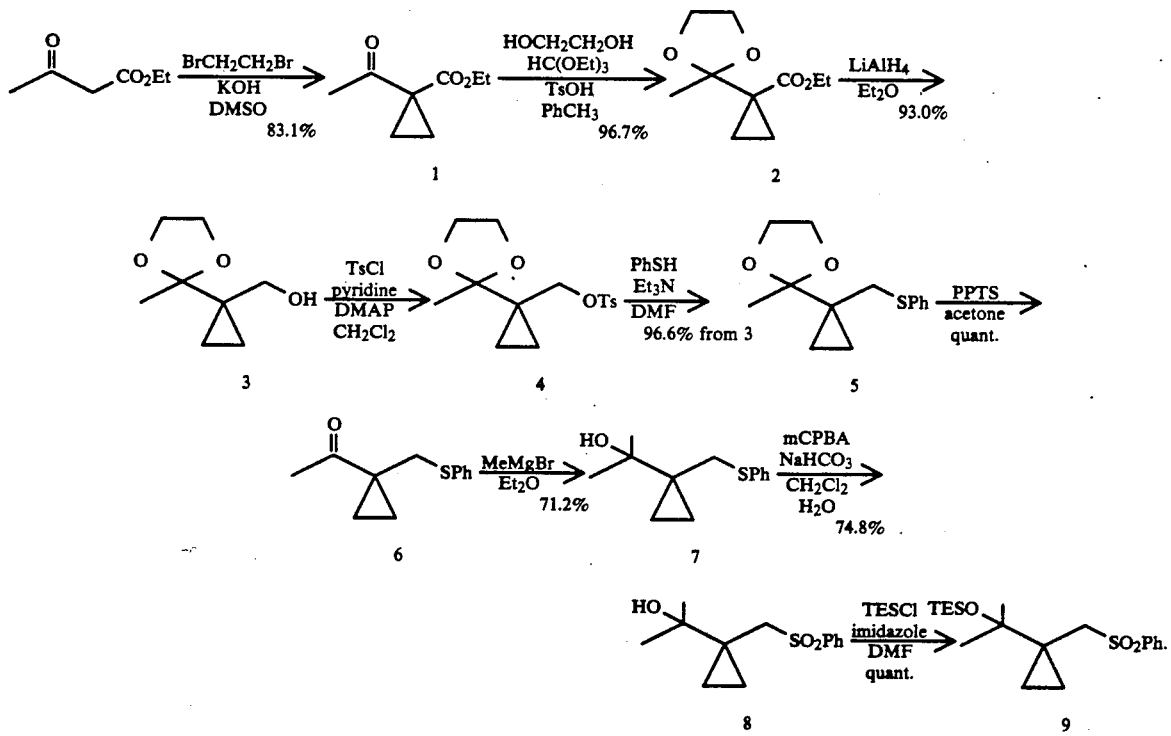

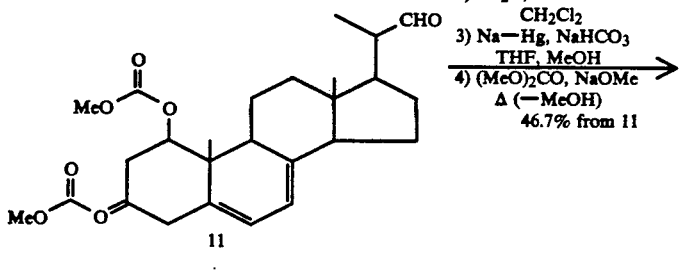

5,194,431
-continued
PROCESS SCHEME I
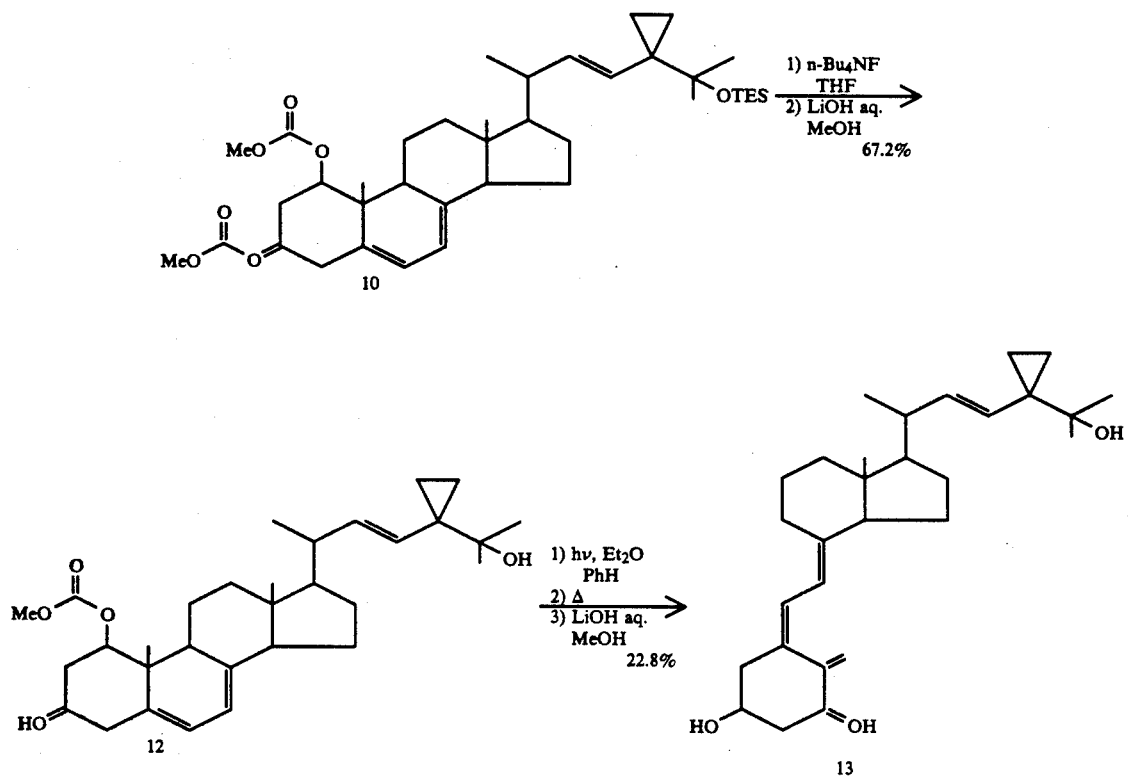
PROCESS SCHEME II
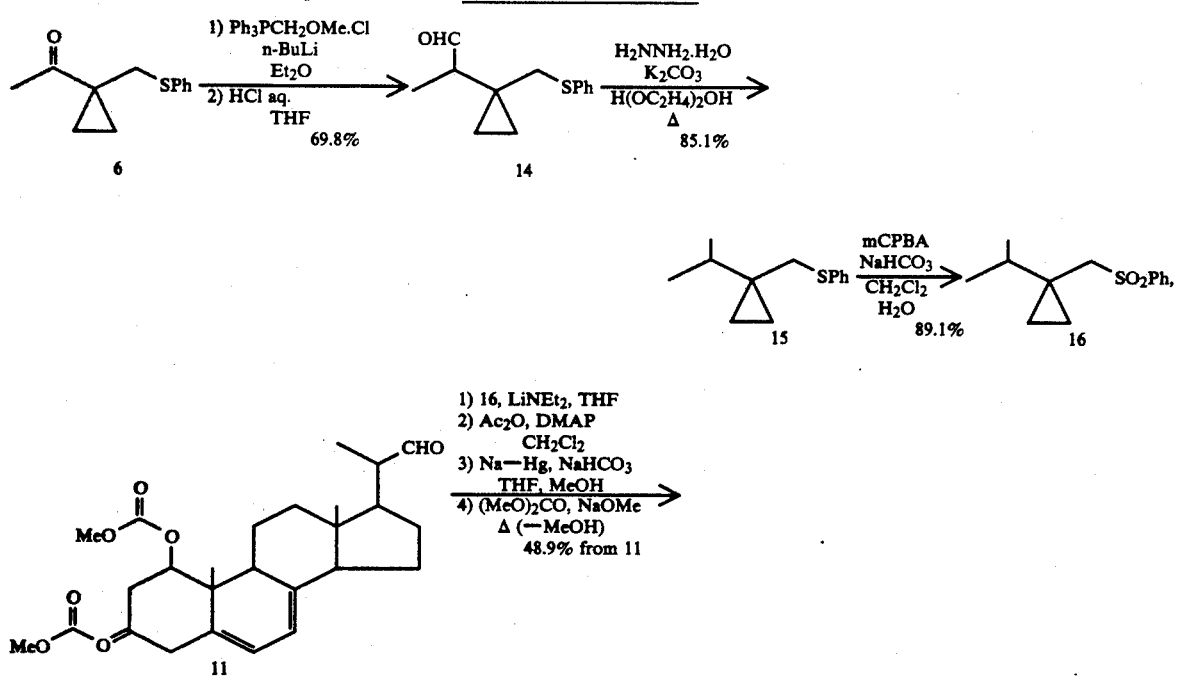

PROCESS SCHEME II
−continued

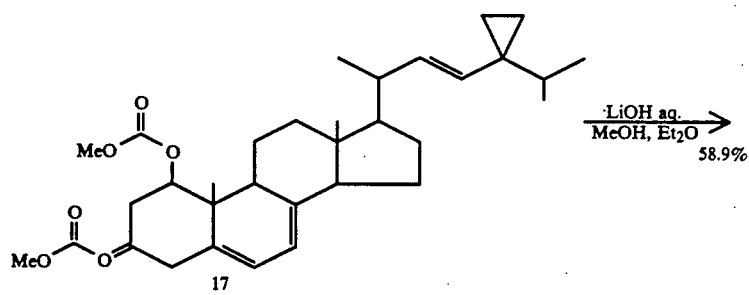

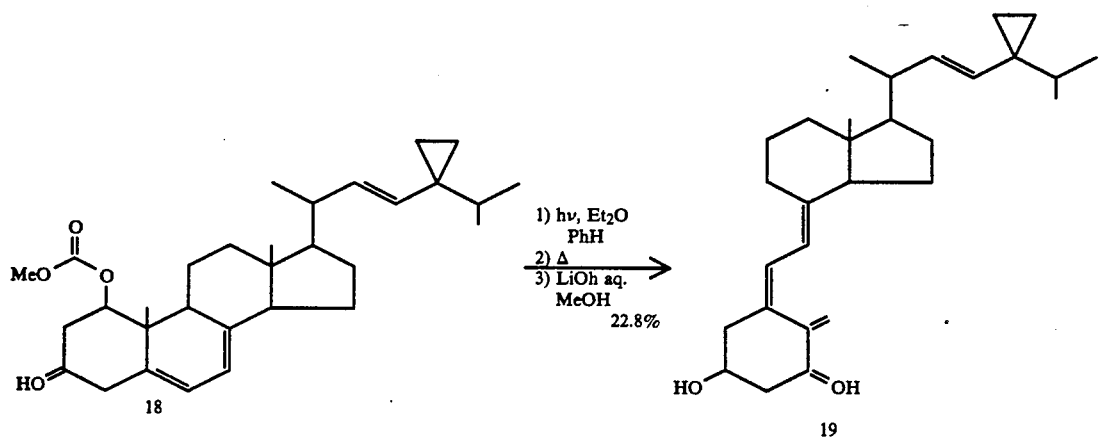

We claim:
1. A compound having the formula

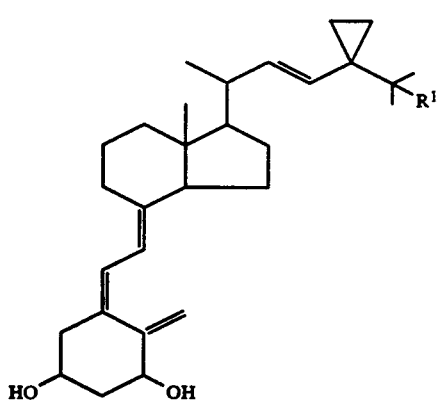

where R[1] is hydrogen or hydroxy.
2. 24,28-methylene-1α,25-dihydroxyvitamin $D_2$.
3. 24,28-methylene-1α-hydroxyvitamin $D_2$.
4. A method of treating metabolic bone disease where it is desired to maintain or increase bone mass comprising administering to a patient with said disease a compound having the formula

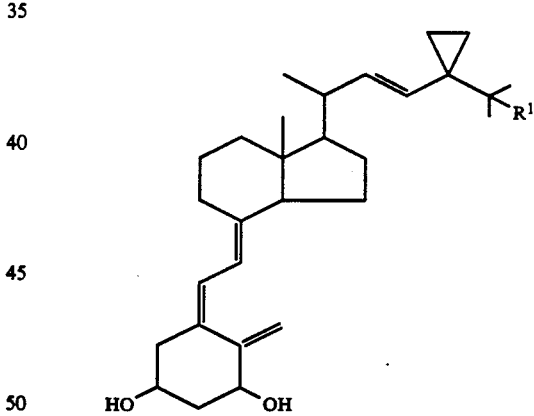

where R[1] is hydrogen or hydroxy.
5. The method of claim 4 where the disease is osteoporosis.
6. The method of claim 4 where the disease is osteomalacia.
7. The method of claim 4 where the disease is renal osteodystrophy.
8. The method of claim 4 wherein the compound is administered orally.
9. The method of claim 4 wherein the compound is administered parenterally.
10. The method of claim 4 wherein the compound is administered transdermally.
11. The method of claim 4 wherein the compound is administered in a dosage of from 0.5 μg to 50 μg per day.
12. A compound having the formula

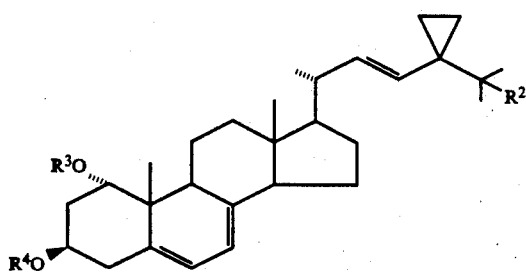

where $R^2$ is hydrogen or hydroxy, $R^3$ is a hydroxy-protecting group and $R^4$ is hydrogen or a hydroxy-protecting group.

13. The compound of claim 12 where $R^2$ and $R^4$ are both hydrogen and $R^3$ is a hydroxy-protecting group.

14. A pharmaceutical composition containing at least one compound as claimed in claim 1 together with a pharmaceutically acceptable excipient.

15. The pharmaceutical composition of claim 14 containing 24,28-methylene-1α,25-dihydroxyvitamin $D_2$ in an amount from about 0.5 μg to about 50 μg.

16. The pharmaceutical composition of claim 14 containing 24,28-dimethylene-1α-dihydroxy-vitamin $D_2$ in amount from about 0.5 μg to about 50 μg.

* * * * *

UNITED STATES PATENT AND TRADEMARK OFFICE
CERTIFICATE OF CORRECTION

PATENT NO. : 5,194,431
DATED : March 16, 1993
INVENTOR(S) : HECTOR F. DeLUCA ET AL It is certified that error appears in the above-identified patent and that said Letters Patent is hereby corrected as shown below:

IN PROCESS SCHEME I:

At the bottom of Column 15, replace compound

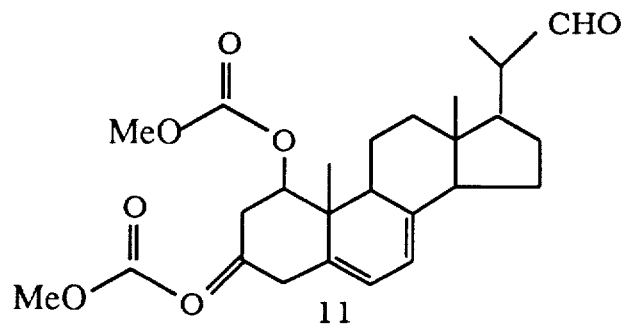

With compound 11

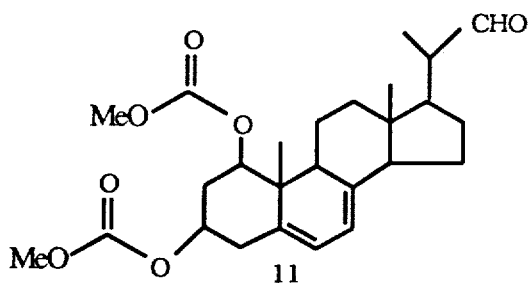

UNITED STATES PATENT AND TRADEMARK OFFICE
CERTIFICATE OF CORRECTION

PATENT NO. : 5,194,431
DATED : March 16, 1993
INVENTOR(S) : HECTOR F. DeLUCA ET AL It is certified that error appears in the above-identified patent and that said Letters Patent is hereby corrected as shown below:

At the top of Column 17 replace compound 10

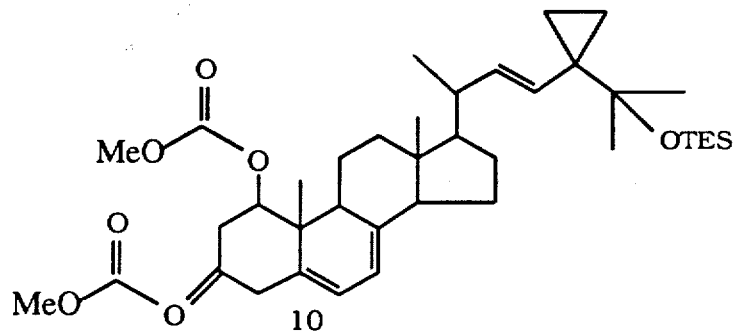

With compound 10

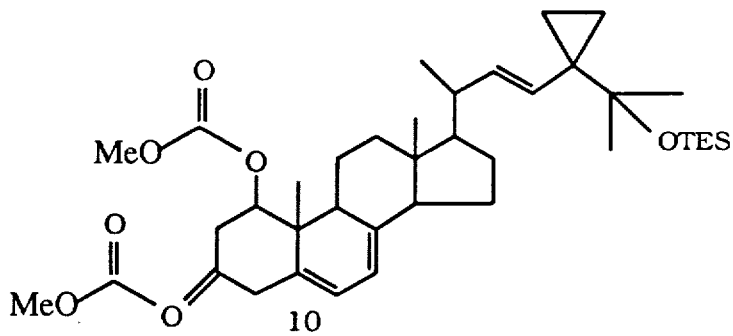

UNITED STATES PATENT AND TRADEMARK OFFICE
CERTIFICATE OF CORRECTION

PATENT NO. : 5,194,431
DATED : March 16, 1993
INVENTOR(S) : HECTOR F. DeLUCA ET AL It is certified that error appears in the above-identified patent and that said Letters Patent is hereby corrected as shown below:

IN PROCESS SCHEME II:

At the bottom of Column 17 replace compound 11

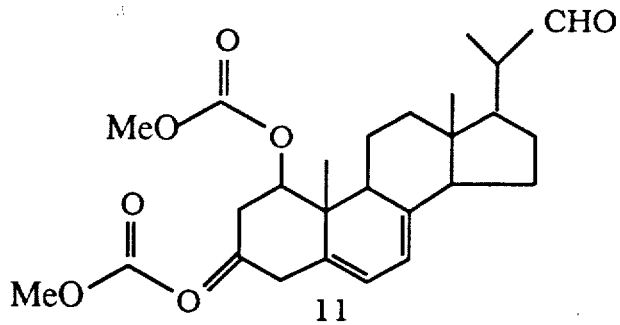

With compound 11

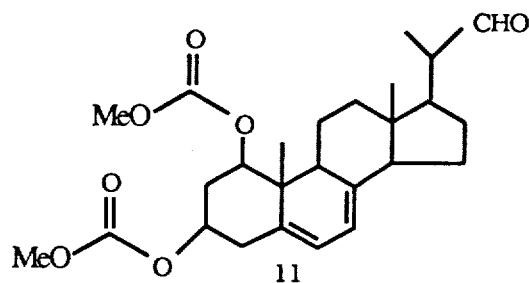

UNITED STATES PATENT AND TRADEMARK OFFICE
CERTIFICATE OF CORRECTION

PATENT NO. : 5,194,431

DATED : March 16, 1993

INVENTOR(S) : HECTOR F. DeLUCA ET AL

It is certified that error appears in the above-identified patent and that said Letters Patent is hereby corrected as shown below:

Midway down Column 17 replace compound 12

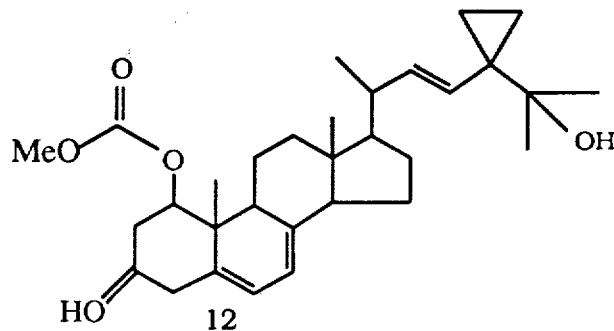

With compound 12

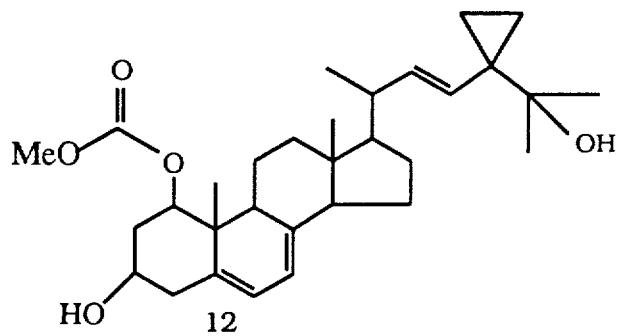

UNITED STATES PATENT AND TRADEMARK OFFICE
CERTIFICATE OF CORRECTION

PATENT NO. : 5,194,431

DATED : March 16, 1993

INVENTOR(S) : HECTOR F. DeLUCA ET AL

It is certified that error appears in the above-identified patent and that said Letters Patent is hereby corrected as shown below:

Midway down Column 18 replace compound 13

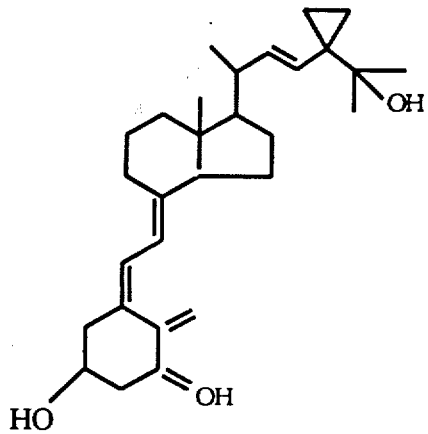

13

With compound 13

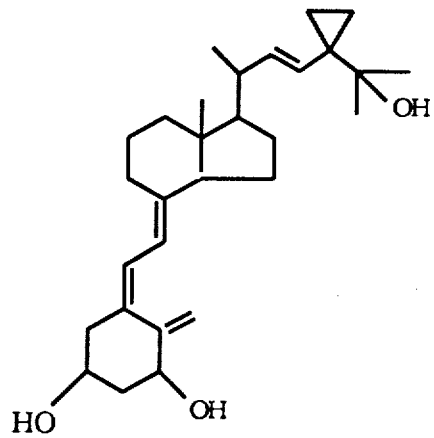

13

UNITED STATES PATENT AND TRADEMARK OFFICE
CERTIFICATE OF CORRECTION

PATENT NO. : 5,194,431

DATED : March 16, 1993

INVENTOR(S) : HECTOR F. DeLUCA ET AL

It is certified that error appears in the above-identified patent and that said Letters Patent is hereby corrected as shown below:

At the top of column 19 replace compound 17

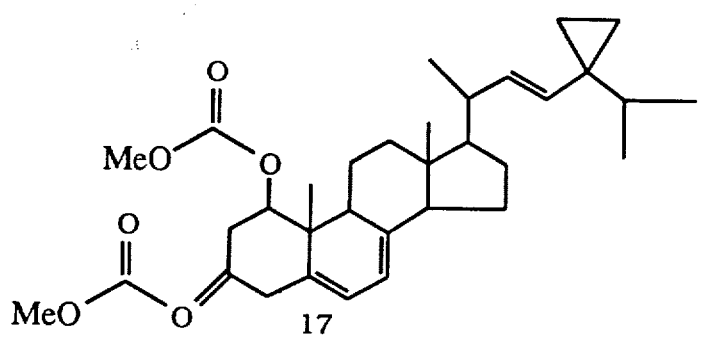

With compound 17

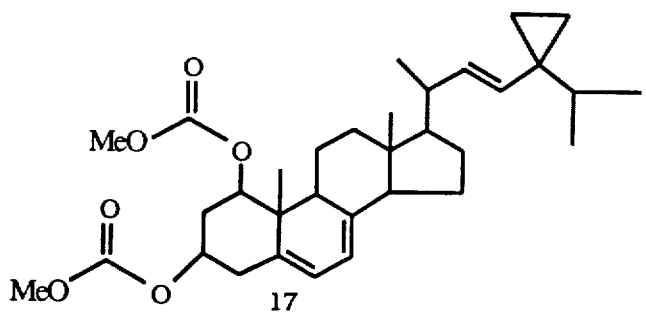

UNITED STATES PATENT AND TRADEMARK OFFICE
CERTIFICATE OF CORRECTION

PATENT NO. : 5,194,431
DATED : March 16, 1993
INVENTOR(S) : HECTOR F. DeLUCA ET AL It is certified that error appears in the above-identified patent and that said Letters Patent is hereby corrected as shown below:

Midway down Column 19 replace compound 18

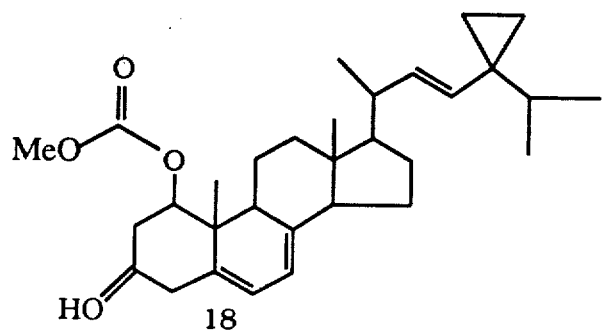

With compound 18

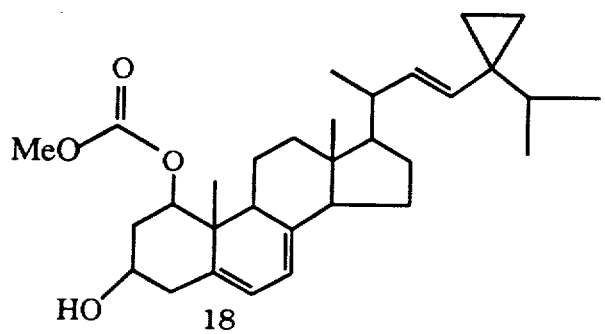

UNITED STATES PATENT AND TRADEMARK OFFICE
CERTIFICATE OF CORRECTION

PATENT NO. : 5,194,431

DATED : March 16, 1993

INVENTOR(S) : HECTOR F. DeLUCA ET AL

It is certified that error appears in the above-identified patent and that said Letters Patent is hereby corrected as shown below:

Midway down Column 20 replace compound 19

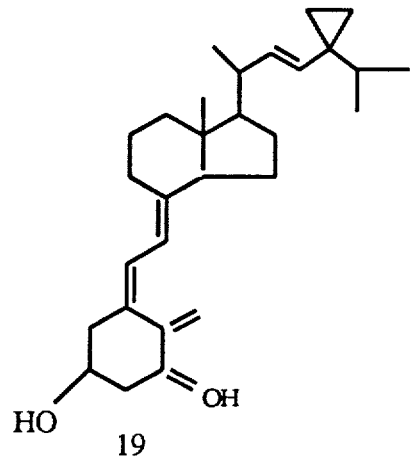

UNITED STATES PATENT AND TRADEMARK OFFICE
CERTIFICATE OF CORRECTION

PATENT NO. : 5,194,431
DATED : March 16, 1993
INVENTOR(S) : Hector F. DeLuca et al It is certified that error appears in the above-indentified patent and that said Letters Patent is hereby corrected as shown below:

With compound 19

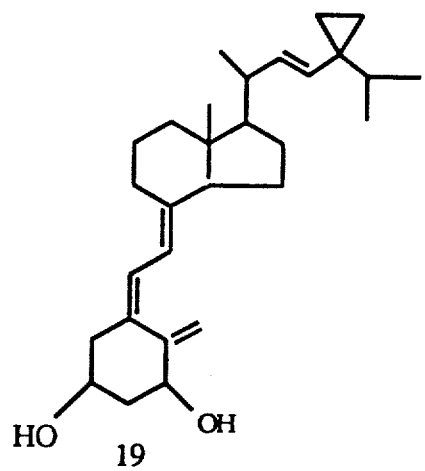

Signed and Sealed this

Twenty-second Day of February, 1994

*Attest:*

BRUCE LEHMAN

*Attesting Officer*     *Commissioner of Patents and Trademarks*